United States Patent
Byers

(12) United States Patent     (10) Patent No.: US 7,290,016 B2
     Byers                                                  (45) Date of Patent:     Oct. 30, 2007

(54) METHOD AND APPARATUS FOR OBTAINING AND STORING MEDICAL HISTORY RECORDS

(76) Inventor: Frank Hugh Byers, 2411 Bugle La., Reston, VA (US) 20191

( * ) Notice: Subject to any disclaimer, the term of this patent is extended or adjusted under 35 U.S.C. 154(b) by 37 days.

(21) Appl. No.: 10/445,788

(22) Filed: May 27, 2003

(65) Prior Publication Data
     US 2004/0243586 A1     Dec. 2, 2004

(51) Int. Cl.
     *G06F 12/00*     (2006.01)
(52) U.S. Cl. ........................... 707/203; 707/200
(58) Field of Classification Search ......... 707/1–104.1, 707/203; 705/1–3; 600/300–301, 481, 513, 600/508–509; 235/380, 375; 283/56, 116, 283/900; 706/902, 924; 713/193, 189; 715/530; 128/920–923, 897
See application file for complete search history.

(56) References Cited

U.S. PATENT DOCUMENTS

| | | | | |
|---|---|---|---|---|
| 3,805,412 A | * | 4/1974 | Lambright et al. | ......... 434/321 |
| 4,130,881 A | * | 12/1978 | Haessler et al. | |
| 5,341,291 A | * | 8/1994 | Roizen et al. | .............. 600/300 |
| 5,572,421 A | * | 11/1996 | Altman et al. | ................ 705/3 |
| 5,724,985 A | * | 3/1998 | Snell et al. | |
| 6,003,020 A | * | 12/1999 | Hazlehurst et al. | |
| 6,026,363 A | * | 2/2000 | Shepard | |
| 6,032,156 A | * | 2/2000 | Marcus | |
| 6,067,523 A | * | 5/2000 | Bair et al. | |
| 6,177,940 B1 | * | 1/2001 | Bond et al. | |
| 6,206,829 B1 | * | 3/2001 | Iliff | |
| 6,269,339 B1 | * | 7/2001 | Silver | |
| 6,270,456 B1 | * | 8/2001 | Iliff | |
| 6,669,630 B1 | * | 12/2003 | Joliat et al. | |
| 6,692,436 B1 | * | 2/2004 | Bluth et al. | ................ 600/300 |
| 6,697,783 B1 | * | 2/2004 | Brinkman et al. | |
| 2002/0315263 | * | 7/2001 | Marchosky | ..................... 705/3 |
| 2001/0034615 A1 | * | 10/2001 | Wilkinson et al. | ............. 705/2 |
| 2002/0023144 A1 | * | 2/2002 | Linyard et al. | ............. 709/218 |
| 2002/0029157 A1 | * | 3/2002 | Marchosky | ..................... 705/3 |
| 2002/0030682 A1 | * | 3/2002 | Eberlein | ..................... 345/440 |
| 2003/0004788 A1 | * | 1/2003 | Edmundson et al. | ......... 705/10 |
| 2003/0050803 A1 | * | 3/2003 | Marchosky | ..................... 705/3 |
| 2003/0065241 A1 | * | 4/2003 | Hohnloser | ..................... 600/1 |
| 2003/0065552 A1 | * | 4/2003 | Rubinstenn et al. | .......... 705/10 |
| 2003/0135095 A1 | * | 7/2003 | Iliff | ............................ 600/300 |
| 2003/0153819 A1 | * | 8/2003 | Iliff | ............................ 600/300 |

OTHER PUBLICATIONS

International Search Report for PCT/US04/17185, mailed Sep. 15, 2004.

* cited by examiner

*Primary Examiner*—Don Wong
*Assistant Examiner*—Linh Black
(74) *Attorney, Agent, or Firm*—Mintz, Levin, Cohn, Ferris, Glovsky and Popeo, P.C.

(57) ABSTRACT

A system and method for taking a medical history uses a questionnaire database in which answers to questions are correlated with subsequent questions. The answers given for the medical history provide a path through the database and a compact form for storage of the medical history. A computerized system is used to access the database for creating or retrieving a medical history.

9 Claims, 3 Drawing Sheets

METHOD AND APPARATUS FOR OBTAINING AND STORING MEDICAL HISTORY RECORDS

BACKGROUND OF THE INVENTION

1. Field of the Invention

The present invention relates to a system and method for generating and storing a medical history. More particularly, it relates to a system and method that incorporates the process of taking the medical history using a database to control the system and the storage.

2. Discussion of Related Art

To make an informed diagnosis of a patient's condition, a physician requires an accurate, complete, and up-to-date medical history of the patient. It can be common for a physician or another trained medical professional (e.g., a nurse, nurse practitioner, or physician's assistant) to take a medical history manually and spend significant time questioning the patient and recording the responses. Responses can then be entered into a computer system and stored in a database for later retrieval and review by a medical professional. However, significant time is spent by highly trained medical personnel in obtaining basic information that does not necessarily require their expertise. Furthermore, at each subsequent contact between the patient and a medical professional, the entire medical history must be reviewed. There are no systems for easily determining changes in medical histories or analyzing the significance of such changes. As the costs of health care have increased, the medical industry has sought ways to reduce costs. Therefore, a need exists for a system that can be used to take a medical history without the direct participation of expensive medical personnel. A need further exists for a system that can aid the medical personnel in locating and understanding changes in a medical history of a patient over time.

Some computerized systems are available for patients to enter medical data themselves in response to queries. However, such systems have not yet found widespread acceptance due to limitations in such systems. Typically, a computerized medical history system uses a predetermined set of questions for the patient to answer. Many times, the answers to certain questions require additional information or follow up, which then must be performed by medical personnel. Sometimes, test information is needed in response to questions, or test results require additional questions. Furthermore, such systems do not respond to changing facts. Typically, the entire medical history has to be reset and reviewed by the patient upon every occurrence. These systems lack the ability to determine or analyze the parts of the medical history that have changed. Therefore, a need exists for a computerized system that can accommodate and respond to large variations in questioning systems and test information. Typically, the content and order of medical histories are dependent upon the facility where the medical history is taken, or even the particular person who takes the history. There are no standard formats, questions, or organization. Thus, even if a medical history were obtained from another location, it might not be easily transferable to the new system. This problem is further exacerbated by differences in languages, which prevent even simple translations.

Once a medical history is taken, it is typically stored in a database of the computer system of the medical facility where the history was taken. A disadvantage of this method for storing medical records is that the databases are not easily accessible. The records can be retrieved only by medical professionals within a particular office, facility, or care network. When a patient is "out of network" and has an emergency, the medical personnel treating the patient in that emergency often do not have access to the patient's medical history. Additionally, when a patient has various medical needs and must go to another facility, personnel in that facility may be required to do a complete medical history again. Even if the information could be retrieved by other facilities, there may be additional problems when medical records are in a language other than that of the health care provider, or are stored in an unknown format. Therefore, a need exists for a system that permits simplified access to a medical history for a patient at different locations and different times.

Another issue with computerized medical records relates to the sheer size of the data being stored, especially medical image data. The size of the data being stored can be a limitation when attempting to provide patient data via a mechanism such as a so-called "smart card" that the patient can carry. It would be desirable to store at least some of a patient's medical history in a form that takes up very little memory, while still providing a full range of information about the patient. Therefore, a need exists for a system for storing a medical history with minimal memory requirements.

One proposed solution to improving access to and increasing storage for medical records has been storing of medical records online. As health care has been increasingly computerized and as the Internet has become prevalent as a means of communicating information, the Internet is being used to collect, analyze, and distribute medical data. Online medical history information enables patients and their health care providers to access medical history information such as recent treatments, medical test results, medical images (e.g., X-Ray, CAT Scan, MRI, etc.), family histories, and the like. Despite the advantages of online availability of medical data, there are unresolved issues, including controlling the use of and access to the information and determining ownership of the information. The Congress of the United States has similar concerns with the use of medical record information, and the Health Insurance Portability and Accountability Act of 1996 (HIPAA) required Congress to pass requirements for medical record privacy. Thus, there is a need for systems that can provide improved confidentiality of online medical records such as medical histories. Even without online records, privacy is a major concern with many systems. A third-party payor may review a medical history in determining proper treatment, tests, diagnosis, and other matters necessary for authorization of payment. Under known systems, the private medical information of a patient is provided to and reviewed by clerical personnel at the payor. No system exists for providing necessary information for making payment decisions without disclosing private medical records.

SUMMARY OF THE INVENTION

The present invention substantially overcomes the deficiencies of the prior art by providing a computerized system and method for taking and storing a medical history utilizing a questionnaire database based upon patterns of responses. According to one aspect of the invention, the questionnaire database includes a plurality of questions and corresponding multiple-choice responses. The responses are associated with additional questions in the questionnaire database.

Thus, a subsequent question is retrieved and presented to the user based upon the answer to the proceeding question. Therefore, the pattern through the questionnaire database is not predetermined, but is dependent upon the pattern of answers.

According to another aspect of the invention, the questionnaire database is used to store the medical history in a manner that is confidential, compact, and easily transferable. The medical history is stored as the sequence of answers to the questions, without reference to the questions themselves. Since subsequent questions depend upon the prior answers, the stored answers provide a history path through the questionnaire database. Without the database, the stored medical history has no meaning. It can only be interpreted with the proper database. Access to the database, necessary for interpreting the stored history, can be controlled by appropriate safeguards. However, a medical history can easily be retrieved if the database is available. Furthermore, the medical history can be easily converted into another language by using a corresponding database in the other language. Furthermore, by using the answers to multiple-choice questions, the medical history can be stored in a compact form as a sequence of single digits.

According to another aspect of the invention, a system for processing medical records includes a questionnaire database, a user interface, a processing subsystem, and a storage device. The processing subsystem operates with the questionnaire database to control the acquisition, storage, and retrieval of data relating to medical histories. The processing subsystem presents questions from the questionnaire database to the use through the user interface. The selected multiple-choice response to a question is stored, and the next question retrieved based upon the response. The storage device stores history path information that is associated with a patient. The user interface is a browser-based interface enabling users (including doctors and patients) to interact with information in the questionnaire database and in the storage device. The user interface includes a patient portion that requests responses to questions from the questionnaire database. The answers are stored and the subsequent questions retrieved. The user interface includes a doctor portion that allows a doctor to use the database to review a medical history. The stored answers are used to follow the path through the database and create the medical history.

According to another aspect of the invention, medical information is stored in a confidential manner. This may be accomplished by storing only history path information to represent a patient's medical history. The history path information does not disclose a patient's medical history, without use of the questionnaire. Access to the conversion system, which includes the questionnaire and branching information, is controlled to provide security for the patient's medical records. In addition, storing history path information, rather than the actual medical record itself can help to decrease the amount of memory required to store the medical record.

The collection and storage of medical history information as a history path enables a flexible system that allows efficient use and review of medical information. According to one aspect of the invention, the medical history can be reviewed automatically for coding for billing purposes or for review for payment. The third party payor can review a history to determine medical necessity without disclosure of the personal medical information to clerical personnel. According to another aspect of the invention, the system can automatically compare medical histories created over time. The changes, which would be of most significance in diagnosis, can be provided in a coherent manner to the medical personnel. Thus, the in-person time of expensive medical personnel can be focused on the most relevant matters. The use of the medical history path provides information regarding patterns in the responses for improved analysis. According to another aspect, the medical history can be reviewed easily for changing medical facts. The medical history path can be compared to the prior path to determine areas of separation. These areas can be presented to the medical personnel for improved diagnosis.

According to another aspect of the invention, the system includes a set of libraries associated with medical histories. The libraries provide a great level of flexibility in creation and use of medical histories. Different entities may utilize different libraries with the same medical history. Libraries may include additional textual information for the patient during the taking or review of the medical history, textual information for medical personnel in reviewing a history, coding information for triage or billing purposes, and links to additional information relevant to a particular history, including test results. According to another aspect of the invention, the system may use the medical history and libraries to determine recommended physical tests. These tests can be performed following the medical history session even before the history has been reviewed by medical personnel. In this manner, the use of medical personnel is optimized since all basic testing, based upon the medical history, can be performed before the first review.

BRIEF DESCRIPTION OF THE FIGURES

The advantages and aspects of the present invention will be more fully understood in conjunction with the following detailed description and accompanying drawings, wherein.

DETAILED DESCRIPTION

The system of the present invention is implemented in a computer. Any type of general purpose computer system can be used, such as a personal computer (PC), laptop computer, server, workstation, personal digital assistant (PDA), mobile communications device, interconnected group of general purpose computers, and the like, running any one of a variety of operating systems. Alternatively, the system could be implemented on a special purpose computer or computer network specifically created to perform the functions of the present invention. Preferably, the system of the present invention includes a network of computers that can share data. In this manner, medical histories can be created and retrieved at various locations. In another preferred embodiment, the system of the present invention is implemented on a server system connected to a worldwide network, which can be accessed from any location connected to the network. In such an embodiment, the system may include an ASP associated with the questionnaire database, which is accessed by a user interface associated with a client browser. Different hardware and software configurations, including types of computers, networks, and operating systems, will be readily apparent to those of skill in the art of computer programming based upon the functions and capabilities of the system of the present invention.

Figure 1:
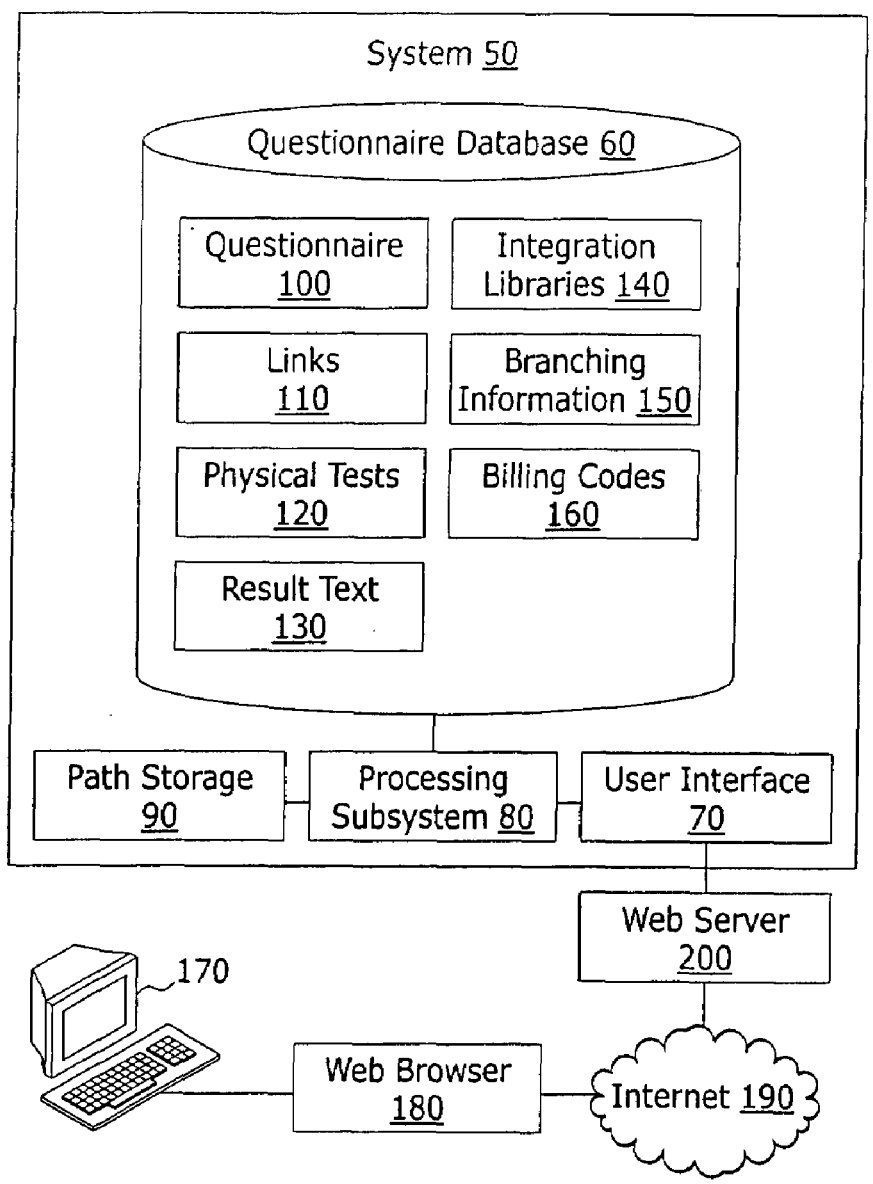
FIG. 1 is an illustrative block diagram of a system implemented in accordance with an embodiment of the invention.

FIG. 1 is an illustrative block diagram of a system 50 implemented in accordance with an embodiment of the invention. The system 50 includes a questionnaire database 60, a user interface 70, a processing subsystem 80, and path storage 90. A user 170 interacts with the system 50 via a web browser 180 accessible to the user 170. The web browser 180 interacts over a computer network 190, such as the Internet, with a web server 200 in communication with the system 50. Of course, it is not necessary to access the system 50 over the Internet. For example, in at least one embodiment, the user 170, using a browser such as the web browser 180, can directly access with the system 50. In another example, the user 170 can access the system 50 through a computer network 190 other than the Internet.

The user interface 70, in one embodiment, is a browser-based application that works with the processing subsystem 80 to perform the functions of the system. In particular, the system is used to access the questionnaire database for creation or retrieval of medical histories. The processes for creating and retrieving medical histories are set forth in detail below. Furthermore, the system may, either through the user interface or the processing subsystem provide desired security for the system. Medical records must be kept confidential. The system should include appropriate functionality to prevent unauthorized access to the system or to specific patient medical records. Also, since the medical records are stored as path information, access to the questionnaire database is necessary and sufficient for interpreting the medical history. Thus, access to the questionnaire database must be controlled. Accordingly, security measures, such as the use of usernames, passwords, and access control, is implemented in the user interface or processing subsystem of the present invention.

The questionnaire database 60 is used for storing all of the information necessary to create and retrieve medical histories. The questionnaire database 60 may be organized in various manners. FIG. 1 illustrates subsets of the contents of the questionnaire database according to an embodiment of the present invention. As illustrated in FIG. 1, the questionnaire database 60 comprises a questionnaire 100, links 110, physical tests 120, result text 130, integration libraries 140, branching information 150, and billing codes 160.

The questionnaire 100 is, in one embodiment, a set of multiple-choice questions and responses that are designed to take information relating to a patient's medical history. Each question in the questionnaire can be identified by version (e.g., by a version and sub-version identifier). Thus, if a question and/or its responses are changed over time, those obtaining the branch information and viewing the resultant medical history at a later date will be able to properly reconstruct the meaning of certain responses, based on the version identification information. If necessary, the questionnaire 100 can be prepared in multiple language version sets, such that any text component can be mapped to a corresponding component in a different language set. This enables information to be usable even if it was taken in a different language. Associated with each of the possible responses to questions in the questionnaire 100 are links 110, physical tests 120, result text 130, integration libraries 140, branching information 150, and/or billing codes 160.

The links 110 are links to information (e.g., educational information) that may be relevant to a particular question and/or response. For example, the links may be links to places on a computer network, such as websites, containing more information about the question and/or response. A given link 10 can, for example, be provided to a person taking a questionnaire based on the person's answers to one or more questions. The physical tests 120 constitute one or more physical tests that may be suggested to a user based on one or more responses to a question in the questionnaire 100.

In particular, the questionnaire database 60 includes a set of questions and associated responses selectable by the user. Each response correlates to additional questions, tests or information. Table 1 illustrates a questionnaire database of six questions. Of course, an embodiment of the present invention would likely have thousands of questions. Associated with each question in the database is a set of responses. As illustrated in Table 1, there are three responses for each question. However, the present invention is not limited to three responses, nor to the same number of responses for each question. Each response also includes a link to the next step. The next step may be another question (Q2) or a potential diagnosis (DX1), as illustrated in Table 1. The diagnoses are set forth in Table 2 and would be included in the links portion of the questionnaire database 60. Although not illustrated in the simplified example of Table 1, responses may be associated with desirable physical tests to be performed, or with other information. Furthermore, the results of physical tests may be included within the responses to a question, as appropriate. Given the table format of the questions and responses as illustrated in Table 1, the questionnaire database may be implemented as a relational database. Of course, any other type of database or organizational structure may be used.

TABLE 1

| Question No. | Query | Response 1 | Response 2 | Response 3 |
|---|---|---|---|---|
| 1 | Have you been coughing continually? | Yes, and my coughing has been going on for more than 2 months and/or has been getting worse DX1 | Yes, once in a while I have a period where I cough continually, but it doesn't last more than a few weeks Q2 | No, I'm either not coughing or my coughing is infrequent Q2 |
| 2 | Do you smoke? | Yes, currently a smoker Q3 | No, but used to smoke Q4 | No, non-smoker and never smoked Q4 |
| 3 | How many cigarettes a day do you smoke? | 1 or more packs a day Q5 | ½ pack to 1 pack a day Q5 | Less than ½ pack a day Q3 |

TABLE 1-continued

| Question No. | Query | Response 1 | Response 2 | Response 3 |
|---|---|---|---|---|
| 4 | Do you have trouble breathing? | Yes, most of time Q5 | Yes, sometimes Q6 | No Q6 |
| 5 | Have you been fatigued? | Yes, most of time DX1 | Yes, sometimes Q6 | No DX3 |
| 6 | Have you lost weight recently without trying? | Yes, I've lost weight and I have no appetite. DX1 | Yes, I've lost weight even though I still have an appetite. DX2 | No, no unexplained weight loss DX3 |

TABLE 2

| | |
|---|---|
| DX1 | Possible screen for lung cancer; order X-ray, set up appointment with pulmonologist |
| DX2 | Possible screen for chest problems, possible lung cancer; order X-ray and review results |
| DX3 | Monitor patient, encourage smoking cessation (if applicable); if coughing continues, repeat exam |

Figure 2:
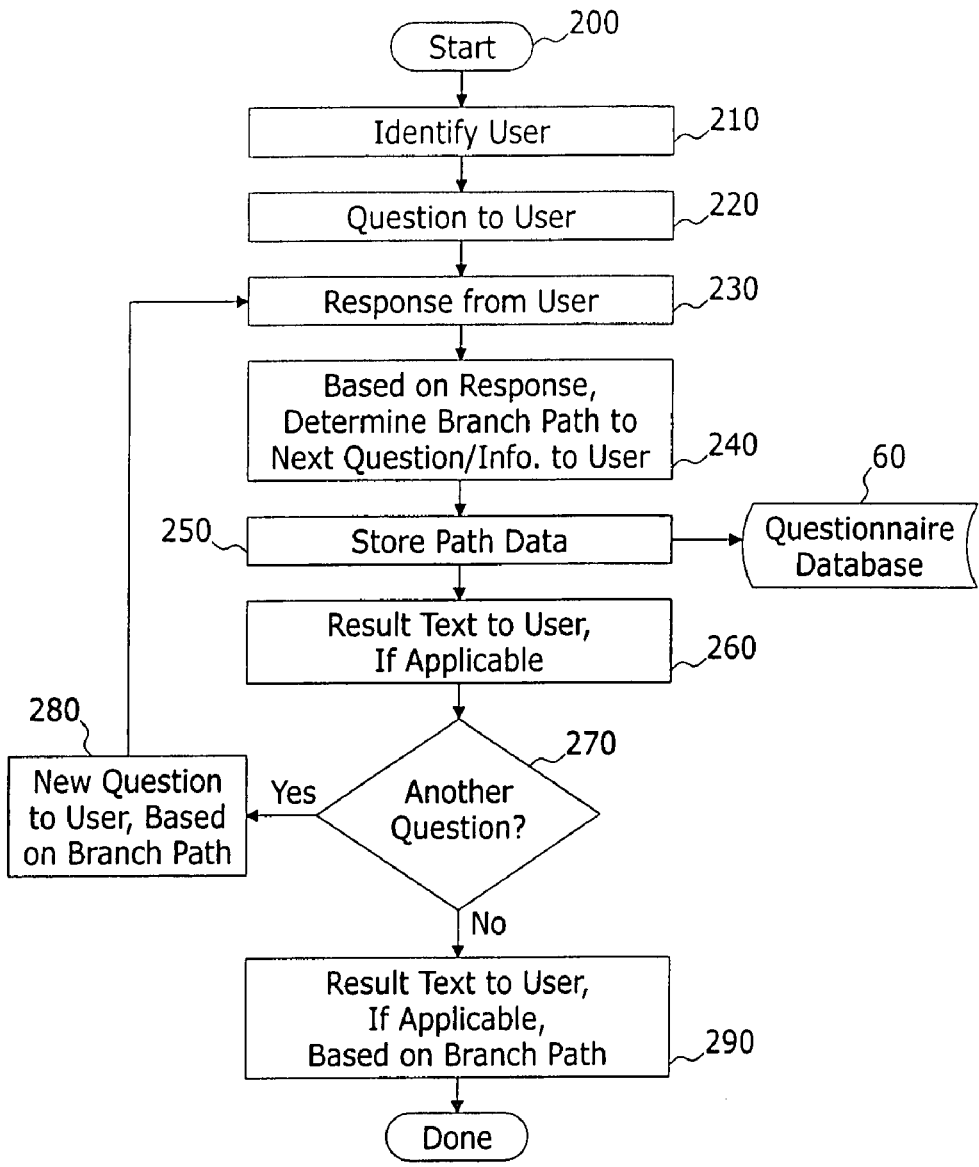
FIG. 2 is a flowchart illustrating a method for taking a medical history, in accordance with an embodiment of the invention.

FIG. 2 illustrates a process for creating a medical history according to an embodiment of the present invention. At step 210, information identifying the user is entered. This may include a name, an identifier, or other information. It may also require entry of a password to prevent unauthorized access. At step 220, the first question is presented to the user along with the associated responses. The processing subsystem and user interface would interact to provide the question and response in an appropriate manner for review and response by the user. At step 230, the user inputs the response, namely, the number of the appropriate response from the database. Again the processing subsystem and user interface interact to receive the response from the user. At step 240, the questionnaire database 60 is used to determine the branch path associated with the selected response. The selected response is stored as a path for the medical history at step 250, and the next question or information is retrieved. If appropriate, additional information or text is presented to the user at step 260. If the selected response correlates to another question, then the system retrieves and presents the next question. The process continues until an end point is reached. As each question is presented, the response is stored as part of the history path. When completed, the history path provides a complete medical history for the user.

The operation of the system will be illustrated with respect to the simplified questionnaire database shown in Table 1. Table 3 illustrates history paths for users in the system of Table 1. In response to the first question, Jones answered for the first response. The first response is associated with a recommendation and no additional questions. Thus, for Jones, the recommendation is presented and the process ends. The history path for Jones consists of a single value, 1, meaning the first response to the first question.

TABLE 3

| Patient | History Path |
|---|---|
| Jones | 1 |
| Smith | 2323 |

TABLE 3-continued

| Patient | History Path |
|---|---|
| Nelson | 31136 |
| Adams | 3333 |

Smith selected response 2 to the first question, and received additional questions. Since response 2 is associated with question 2, that question would be presented to Smith. In response to question 2, Smith selected response 3, which is associated with question 4. In response to question 4, Smith selected response 2, which is associated with question 6. In response to question 6, Smith selected response 3, which is associated with diagnosis 3. At this point, Smith has reached the end of the questions and the history path is complete. Smith was never presented with questions 3 or 5. The history path itself does not indicate the questions that are being answered. Thus, the history path is meaningless without the questionnaire database and the branching information therein.

The number of entries in a history path is dependent upon the responses and the branching information in the database. As illustrated in Table 3, Nelson answered five questions on his path, while all of the others answered fewer.

Figure 3:
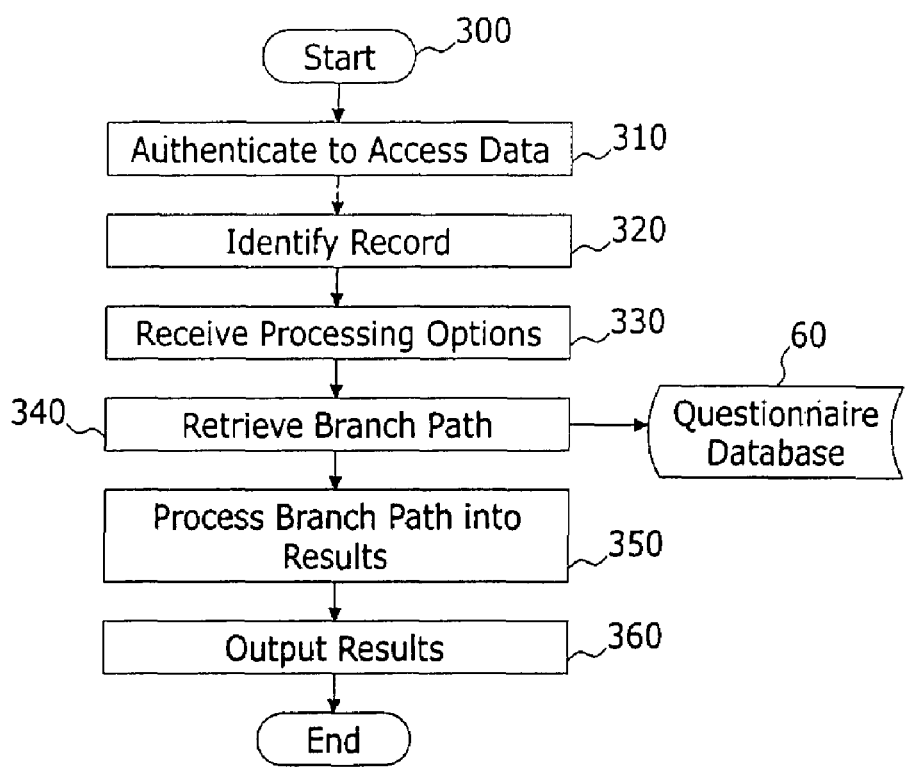
FIG. 3 is a flowchart illustrating a method for retrieving medical information from the system of FIG. 2, in accordance with one embodiment of the invention.

FIG. 3 illustrates the process for recreating a medical history from the history path. The medical history is stored simply as the path. In order for medical personnel to review the medical history, it needs to be recreated from the path. At step 310, the user is authenticated for access to the data. Appropriate security is required to protect patient privacy. At step 320, a record is identified and retrieved. The record corresponds to a history path. At step 330, processing options are received. The processing options may include the version of the database used to create the history path. Since databases may be changed, the version used is necessary to recreate the history. At steps 340 and 350, the branching information is used, in connection with the history path to retrieve the entire medical history. Each entry in the history path is used with the database to determine the response and next question. After the path has been traversed, the entire medical history, including all of the questions answered and the results, has been recreated. At step 360, the medical history can be outputted in a desired form for use by the medical professional.

The medical history of the present invention is easily translated into different formats. Since the questionnaire provides a standardized basis for determining the medical history, any system can convert the information into a desired format. Additionally, the questions and responses can be translated into different languages. Thus, medical personnel can easily interpret the medical history in an appropriate language, independent of the primary language of the patient.

FIG. 3 illustrates one embodiment of a system for recreating the medical history. Storage of the medical history in the form of a history path provides great flexibility to the system of the present invention. The medical history may be recreated and transmitted in a form useful to a specific user. As shown in FIG. 2, the system includes sets of links 110, physical tests 120, integration libraries 140, and billing codes 160. These elements are associated with various parts of the questionnaire 100, response text, or branching information. The appropriate integration library 140 or other reference material to be presented with the medical history may depend upon the objectives of the particular user. For example, for a patient, additional information may include text messages relating to potential diagnoses, treatments, or links to external information such as disease-specific websites or support groups. For physicians, additional information may include medical information on diagnosis, treatments, or prescriptions. Furthermore, the system may use the information in the medical history to highlight changes from previous histories. For billing or payor personnel, the system includes billing codes associated with the questionnaire and responses. The system can automatically create billing requests or review them for payment, without the need for extensive disclosure of personal medical information. Thus, the selection of specific integration libraries and their related content provides great flexibility in use of the system. The underlying feature of any use of the medical history is the relationship between the history path and the questionnaire. The questionnaire, with its branching information, provides the conversion capability of reading the history path in different manners depending upon the needs of the particular user of the medical history.

Furthermore, the format of a medical history according to an embodiment of the present invention allows medical personnel to make meaningful comparisons of changed facts. In obtaining a revised history, the system presents the patient with the former answers and passes through the questionnaire in the same manner as the original medical history. When an answer is changed, the paths diverge and a new set of questions, and corresponding responses, are provided based upon the changed information. Thus, the system determines changed facts and obtains additional information relevant to those changed facts. Medical personnel can quickly review the two histories to determine where changes occurred. This information may be useful in making a new diagnosis or recommendation or modifying a prior one.

The system of the present invention is not limited to medical applications, but can be used for any application that can be simplified into a form of questions with response and branching information. The system of the present invention allows information to be collected and efficiently stored in a secure manner. The information can then be utilized in various manners by different users based upon associated information in the integration libraries.

As those skilled in the art will recognize, the invention described herein can be modified to accommodate and/or comply with any one or more of the above-described technologies and standards. In addition, variations, modifications, and other implementations of what is described herein can occur to those of ordinary skill in the art without departing from the spirit and the scope of the invention as claimed. Further, virtually any aspect of the embodiments of the invention described herein can be implemented using software, hardware, or in a combination of hardware and software.

It should be understood that, in the figures of this application, in some instances, a plurality of system elements or method steps may be shown as illustrative of a particular system element, and a single system element or method step may be shown as illustrative of a plurality of a particular systems elements or method steps. It should be understood that showing a plurality of a particular element or step is not intended to imply that a system or method implemented in accordance with the invention must comprise more than one of that element or step, nor is it intended by illustrating a single element or step that the invention is limited to embodiments having only a single one of that respective elements or steps. In addition, the total number of elements or steps shown for a particular system element or method is not intended to be limiting; those skilled in the art will recognize that the number of a particular system element or method steps can, in some instances, be selected to accommodate the particular user needs.

Although the invention has been described and pictured in a preferred form with a certain degree of particularity, it is understood that the present disclosure of the preferred form, has been made only by way of example, and that numerous changes in the details of construction and combination and arrangement of parts may be made without departing from the spirit and scope of the invention as hereinafter claimed.

The invention claimed is:

1. A method of producing and utilizing a medical history, comprising: presenting a user with a questionnaire including questions with each of the questions including question text;
   receiving selections from the user corresponding to the questions, wherein the selections are stored in a medical history without the question text;
   storing, in the medical history, questionnaire version information including a questionnaire version identifier and a question sub-version identifier for each question presented to the user;
   storing at least one medical history processing algorithm, wherein the questionnaire version information is necessary for the execution of the medical history processing algorithm;
   producing a medical history report from a combination of at least one of the selections in the medical history and the at least one medical history processing algorithm.

2. The method of producing and utilizing a medical history according to claim 1, wherein the selections are ordered; and wherein storing the selection includes storing order information corresponding to the order of the selections from the user.

3. The method of producing and utilizing a medical history according to claim 1, further comprising:
   retrieving the selections stored in the medical history; and
   determining the questionnaire and the question text associated with the selections in the medical history.

4. The method of producing and utilizing a medical history according to claim 1, further comprising:
   linking at least one of the selections from the user with additional information; and
   providing the additional information to the user in response to the at least one selection being made.

5. The method of producing and utilizing a medical history according to claim 4, further comprising determining a category for the user; and wherein the additional information is applicable to the category of the user.

6. The method of producing and utilizing a medical history according to claim 1, further comprising:
- associating at least one physical test with at least one of the selections from the user; and
- recommending that a patient have the at least one physical test done in response to the at least one of the selections from the user being made.

7. A method of storing information, comprising:
- presenting a user with a questionnaire having a plurality of questions and associated available responses, wherein each of the associated responses dictates a subsequent question and each of the questions includes question text;
- receiving actual responses, from the available responses, from the user;
- presenting subsequent questions based upon the actual responses;
- storing a set of values representing the actual responses, without storing the associated question text with the set of values;
- storing a version value representing the particular questionnaire;
- storing a sub-version value for each question presented to the user;
- storing a medical report generator; and
- initiating the medical report generator, wherein the medical report generator receives as an input the version value representing the particular questionnaire, the sub-version value for each question presented to the user, and at least one value in the set of values representing the actual responses, and outputs a medical report.

8. The method of storing information according to claim 7, wherein the responses associated with each of the plurality of questions are ordered; and wherein the set of values corresponds to the order of the responses.

9. The method of producing and utilizing a medical history according to claim 1, further comprising presenting subsequent questions based upon the previous selections.

* * * * *